United States Patent
Watson, III et al.

(10) Patent No.: US 7,438,806 B2
(45) Date of Patent: *Oct. 21, 2008

(54) AFFINITY MATRICES WITH ENHANCED VISIBILITY FOR MOLECULAR PULL-DOWN AND IMMUNOPRECIPITATION APPLICATIONS

(75) Inventors: Edward B. Watson, III, St. Louis, MO (US); Kenneth E. Heuermann, Kirkwood, MO (US); John G. Dapron, St. Louis, MO (US)

(73) Assignee: Sigma-Aldrich Co., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/592,038

(22) Filed: Nov. 2, 2006

(65) Prior Publication Data

US 2007/0048800 A1 Mar. 1, 2007

Related U.S. Application Data

(62) Division of application No. 10/956,825, filed on Oct. 1, 2004, now Pat. No. 7,163,633, which is a division of application No. 10/062,140, filed on Jan. 31, 2002, now Pat. No. 6,887,377.

(60) Provisional application No. 60/267,460, filed on Feb. 8, 2001, provisional application No. 60/265,952, filed on Feb. 1, 2001.

(51) Int. Cl.
*B01D 15/08* (2006.01)

(52) U.S. Cl. .............. 210/198.2; 210/502.1; 210/635; 210/656; 502/402; 502/404

(58) Field of Classification Search .............. 210/635, 210/656, 198.2, 502.1; 502/400, 401, 402, 502/404
See application file for complete search history.

(56) References Cited

U.S. PATENT DOCUMENTS

| | | | |
|---|---|---|---|
| 3,985,620 A | 10/1976 | Karges | |
| 4,016,133 A | 4/1977 | Hyosu et al. | |
| 4,166,105 A | 8/1979 | Hirschfeld | |
| 4,373,932 A | 2/1983 | Gribnau et al. | |
| 4,431,544 A | 2/1984 | Atkinson et al. | |
| 4,546,161 A | 10/1985 | Harvey et al. | |
| 4,605,630 A | 8/1986 | Kung et al. | |
| 4,707,523 A | 11/1987 | Chang et al. | |
| 4,716,219 A | 12/1987 | Eggimann et al. | |
| 4,880,915 A | 11/1989 | Kajihara et al. | |
| 5,030,697 A | 7/1991 | Hugl et al. | |
| 5,135,627 A | 8/1992 | Soane | |
| 5,232,830 A | 8/1993 | Van Ness | |
| 5,395,688 A | 3/1995 | Wang et al. | |
| 5,431,807 A | 7/1995 | Frechet et al. | |
| 5,439,591 A | 8/1995 | Pliura et al. | |
| 5,522,994 A | 6/1996 | Frechet et al. | |
| 5,587,323 A | 12/1996 | Lewis et al. | |
| 5,597,485 A | 1/1997 | Mazza et al. | |
| 5,622,872 A | 4/1997 | Ribi | |
| 5,643,721 A | 7/1997 | Spring et al. | |
| 5,728,457 A | 3/1998 | Frechet et al. | |
| 5,876,597 A | 3/1999 | Mazza et al. | |
| 5,914,241 A | 6/1999 | Valkirs | |
| 6,017,496 A | 1/2000 | Nova et al. | |
| 6,242,185 B1 | 6/2001 | Kaser et al. | |
| 6,428,704 B1 | 8/2002 | Setoguchi et al. | |
| 6,887,377 B2* | 5/2005 | Watson et al. ............ | 210/198.2 |

(Continued)

FOREIGN PATENT DOCUMENTS

EP 0 407 188 A1 1/1991

(Continued)

OTHER PUBLICATIONS

D. Nash et al. "Modification of Polystyrenic Matrices for the Purification of Proteins III. Effects of Poly(vinyl alcohol) modification on the Characteristics of Protein Adsorption on Conventional and Perfusion Polystyrenic Matrices" Journal of Chromatography A, vol. 776 (1997) pp. 55-73.

(Continued)

*Primary Examiner*—Ernest G Therkorn
(74) *Attorney, Agent, or Firm*—Senniger Powers LLP; Jill Rogers-Manning

(57) ABSTRACT

An affinity matrix for use in affinity based molecular pull down and immunoprecipitation procedures. The affinity matrix comprises a polymeric support, a dye attached to a fraction of the polymeric support to enable optical detection of the polymeric support, and an affinity ligand other than the dye attached to a fraction of the polymeric support for the capture of a molecule.

Also provided is a method for the isolation of a biomolecule from an aqueous solution. The method comprises combining the aqueous solution with an affinity matrix comprising a polymeric support and separating the affinity matrix from the aqueous solution. A dye is attached to a fraction of the polymeric support which enables optical detection and monitoring of the affinity matrix and, accordingly, reduces the likelihood of the loss of affinity matrix during the separation step. In addition, an affinity ligand other than the dye is also attached to a fraction of the polymeric support for the capture of the biomolecule.

20 Claims, No Drawings

U.S. PATENT DOCUMENTS 7,163,633 B2 * 1/2007 Watson et al. .............. 210/635

FOREIGN PATENT DOCUMENTS

| EP | 0 455 735 B1 | 11/1991 |
|---|---|---|
| EP | 0 621 074 B1 | 10/1994 |
| GB | 2 097 280 A | 11/1982 |
| JP | 4166767 | 6/1992 |
| WO | WO 84/02193 A1 | 6/1984 |
| WO | WO 90/04609 A1 | 5/1990 |
| WO | WO 94/15951 A1 | 7/1994 |
| WO | WO 97/09068 A3 | 3/1997 |
| WO | WO 97/12994 A1 | 4/1997 |
| WO | WO 98/08603 A1 | 3/1998 |
| WO | WO 99/10370 A1 | 3/1999 |
| WO | WO 00/07024 A3 | 2/2000 |
| WO | WO 00/13706 A1 | 3/2000 |

OTHER PUBLICATIONS

A. Kumar et al. "Polymer Displacement/Shielding in Protein Chromatography" Journal of Chromatography B, vol. 741 (2000) pp. 103-113.

E. Phizicky et al. "Protein-Protein Interactions: Methods for Detection and Analysis" Microbiological Reviews, vol. 59, No. 1 (1995) pp. 94-123.

P. Boyer et al. "Protein Purification by Dye-Ligand Chromatography" Advances in Biochemical Engineering/Biotechnology, vol. 49, pp. 1-44.

P. Dean et al. "Protein Purification Using Immobilized Triazine Dyes" Journal of Chromatography, vol. 165 (1979) pp. 301-319.

G. Gunzer et al. "Purification of $\alpha_1$-Proteinase Inhibitor by Triazine Dye Affinity Chromatography, Ion-Exchange Chromatography and Gel Filtration on Fractogel TSK" Journal of Chromatography, vol. 296 (1984) pp. 221-229.

H. Mottl "Rapid Screening of a Large Number of Immobilized Textile Dyes for the Purification of Proteins: Use of Penicillin-Binding Protein 4 of *Escherichia coli* as a Model Enzyme" Protein Expression and Purification, vol. 3 (1992) pp. 403-409.

M'H. Hasnaoui et al. "Screening of a Large Number of Dyes for the Separation of Human Immunoglobulin G2 from the Other Immunoglobulin G Subclasses Immunoglobulin G2 Enrichment on Immobilized Procion Yellow HE-4R" Journal of Chromatography A, vol. 766 (1997) pp. 49-60.

R. Scopes "Strategies for Enzyme Isolation Using Dye-Ligand and Related Adsorbents" Journal of Chromatography, vol. 376 (1986) pp. 131-140.

R. Nehring et al. "The Metabotropic $GABA_B$ Receptor Directly Interacts with the Activating Transcription Factor 4" The Journal of Biological Chemistry, vol. 275, No. 45 (2000) pp. 35185-35191.

J. Birch et al. "Affinity Chromatography: Its Role in Industry" Biotechnology Applications and Research, Technomic Publishing Company, Inc. Lancaster, PA (1985) pp. 594-606.

C. Lowe et al. "Affinity Chromatography on Immobilized Dyes" Methods in Enzymology, vol. 104, (1984) Chapter 4, pp. 97-112.

D. Stewart et al. "Affinity Chromatography on Triazine Dyes Immobilized on Novel Perfluorocarbon Supports" Journal of Biotechnology, vol. 11 (1989) pp. 253-266.

G. Kopperschlager et al. "Affinity Partitioning: A New Approach for Studying Dye-Protein Interactions" Journal of Chromatography, vol. 376 (1986) pp. 141-148.

R. Delage-Mourroux et al. "Analysis of Estrogen Receptor Interaction with a Repressor of Estrogen Receptor Activity (REA) and the Regulation of Estrogen Receptor Transcriptional Activity by REA" The Journal of Biological Chemistry, vol. 275, No. 46 (2000) pp. 35848-35856.

E. Vignal et al. "Characterization of TCL, a New GTPase of the Rho Family Related to TC10 and Cdc42" The Journal of Biological Chemistry, vol. 275, No. 46 (2000) pp. 36457-36464.

K. Giuliano "Chromatography of Proteins on Columns of Polyvinylpolypyrrolidone Using Absorbed Textile Dyes as Affinity Llgands" Analytical Biochemistry, vol. 200 (1992) pp. 370-375.

C. Jones et al. "Current Trends in Molecular Recognition and Bioseparation" Journal of Chromatography A. vol. 707 (1995) pp. 3-22.

A. Berg et al. "Dye-Ligand Centrifugal Affinity Chromatography" Bioseparation, vol. I, No. 1 (1990) pp. 23-31.

P. Jungblut et al. "Dye Ligand Chromatography and Two-Dimensional Electrophoresis of Complex Protein Extracts from Mouse Tissue" Journal of Chromatography, vol. 482, No. 1 (1989) pp. 125-132.

E. Harlow et al. "Immunoprecipitation" Antibodies: A Laboratory Manual, Cold Spring Harbor Press, NY (1988) Chapter 7, pp. 223-255.

C. Bruton et al. "Large-Scale Purification of Enzymes" Phil. Trans. R. Soc. Lond. B, vol. 300 (1983) pp. 249-261.

J. Noriega et al. "Modeling Column Regeneration Effects on Dye-Ligand Affinity Chromatography" Biotechnology Progress, vol. 13 (1997) pp. 296-300.

D. Nash et al. "Modification of Polystyrenic Matrices for the Purification of Proteins II. Effect of the Degree of Glutaraldehyde-poly(vinyl alcohol) Crosslinking on Various Dye Ligand Chromatography Systems" Journal of Chromatography A, vol. 776 (1997) pp. 55-63.

D. Nash et al. "Modification of Polystyrenic Matrices for the Purification of Proteins III. Effects of Poly(vinyl alcohol) modification on the Characteristics of Protein Adsorption on Conventional and Perfusion Polystyrenic Matrices" Journal of Chromatography A, vol. 776 (1997) pp. 55-73.

A. Kumar et al. "Polymer Displacement/Shielding in Protein Chromatography" Journal of Chromatography B, vol. 741 (2000) pp. 103-113.

E. Phizicky et al. "Protein-Protein Interactions: Methods for Detection and Analysis" Microbiological Reviews, vol. 59, No. 1 (1995) pp. 94-123.

P. Boyer et al. "Protein Purification by Dye-Ligand Chromatography" Advances in Biochemical Engineering/Biotechnology, vol. 49, pp. 1-44, 1993.

P. Dean et al. "Protein Purification Using Immobilized Triazine Dyes" Journal of Chromatography, vol. 165 (1979) pp. 301-319.

G. Gunzer et al. "Purification of $\alpha_1$-Proteinase Inhibitor by Triazine Dye Affinity Chromatography, Ion-Exchange Chromatography and Gel Filtration on Fractogel TSK" Journal of Chromatography, vol. 296 (1984) pp. 221-229.

H. Mottl "Rapid Screening of a Large Number of Immobilized Textile Dyes for the Purification of Proteins: Use of Penicillin-Binding Protein 4 of *Escherichia coli* as a Model Enzyme" Protein Expression and Purification, vol. 3 (1992) pp. 403-409.

M'H. Hasnaoui et al. "Screening of a Large Number of Dyes for the Separation of Human Immunoglobulin G2 from the Other Immunoglobulin G Subclasses Immunoglobulin G2 Enrichment on Immobilized Procion Yellow HE-4R" Journal of Chromatography A, vol. 766 (1997) pp. 49-60.

R. Scopes "Strategies for Enzyme Isolation Using Dye-Ligand and Related Adsorbents" Journal of Chromatography, vol. 376 (1986) pp. 131-140.

R. Nehring et al. "The Metabotropic $GABA_B$ Receptor Directly Interacts with the Activating Transcription Factor 4" The Journal of Biological Chemistry, vol. 275, No. 45 (2000) pp. 35185-35191.

C. Stead "The Use of Dyes in Protein Purification" Bioseparation, vol. 2, No. 3 (1991) pp. 129-136.

J. Scoble et al. "Well Defined Dye Absorbents for Protein Purification" Journal of Molecular Recognition, vol. 9 (1996) pp. 728-732.

Snyder "Characteristics and Use of Different Column Packing" Introduction to Modern Liquid Chromatography (1979) pp. 181-183, John Wiley & Sons, New York.

Mikes, Laboratory Handbook of Chromatographic and Allied Methods (1979) pp. 347-351 and 387-389, John Wiley and Sons, New York.

* cited by examiner

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic FLAG sequence

<400> SEQUENCE: 1

Asp Tyr Lys Asp Asp Asp Asp Lys
1               5
```

AFFINITY MATRICES WITH ENHANCED VISIBILITY FOR MOLECULAR PULL-DOWN AND IMMUNOPRECIPITATION APPLICATIONS

REFERENCE TO RELATED APPLICATIONS

This application is a divisional of U.S. patent application Ser. No. 10/956,825, filed Oct. 1, 2004 now U.S. Pat. No. 7,163,633, which is a divisional of U.S. patent application Ser. No. 10/062,140, filed Jan. 31, 2002, now U.S. Pat. No. 6,887,377, which claims priority from U.S. provisional application Ser. No. 60/267,460, filed Feb. 8, 2001 and Ser. No. 60/265,952, filed on Feb. 1, 2001.

BACKGROUND OF THE INVENTION

Affinity based molecular pull-down (immunoaffinity capture) and immunoprecipitation experiments are powerful and widely used methods to study the expression, modification and interaction of proteins in a wide variety of biological systems. Affinity based molecular pull-down and immunoprecipitation experiments have resulted in the rapid purification of epitope-tagged recombinant proteins, the discovery and characterization of reversible post-translational protein modifications, and a variety of other observations, which have increased the understanding of biological processes at the molecular level.

The underlying strategy behind the affinity based molecular pull-down technique is to use the affinity of biomolecules as a method to select target molecules from a solution. An affinity ligand, such as an antibody, is affixed to a particulate matrix, such as agarose, and the resulting conjugate is used to locate and bind its target, such as a particular antigen, from a biological or biochemical preparation.

Immunoprecipitation is a type of affinity based molecular pull down experiment. Affinity based molecular pull down experiments purify complexes using any affinity ligand that is directly conjugated to a polymeric support having a specific affinity for particular biomolecular targets. However, the general procedures of an affinity based molecular pull down experiment can be illustrated by the procedures involved in an immunoprecipitation experiment. The basic procedure of immunoprecipitation involves three stages. The first stage is preparation of the antigen solution. The second stage is pre-clearing the lysate of nonspecific background, and the third stage is forming and purifying the immune complexes. Once purified, any of a number of methods can be employed to analyze the antigens. The variety of procedures that can be used in affinity based molecular pull down and immunoprecipitation techniques specifically are described in detail in Harlow, E. and Lane, D. (eds.), "Antibodies: a Laboratory Manual", Chapter 7, Cold Spring Harbor Press, NY (1988), the entirety of which is herein incorporated by reference.

Immunoprecipitation is usually performed on a lysate prepared from cells or tissue, although any aqueous solution can be used as a solution for performing an immunoprecipitation. Usually the lysate is prepared from the treatment of cells or tissue with some type of mild detergent. The mild detergent is effective in removing membranes, interfering with many weak intermolecular interactions and releasing most antigens from the cell, without disrupting the conformation or biochemical activity of the antigens of interest. Interferences from nonspecific binding proteins are minimized by pretreating the antigen solution with an antibody that does not bind the antigen of interest to remove the nonspecific binding proteins.

The immune complexes are formed by the addition of specific antibodies to the lysate. Antibodies have high affinity for their respective antigens so the antibody-antigen complexes form rapidly. The complexes are then purified by adding an affinity bead suspension, such as a protein A or protein G bead suspension, to the solution containing the antibody-antigen complexes. The purification occurs because protein A and protein G have a high affinity for the Fc portion of the antibody. After the complex is bound to the bead through the protein A/G-antibody interaction, the beads are collected by centrifugation and the unbound proteins are removed by washing the beads. The beads can be washed by rinsing with a solution such as lysis buffer and removing the lysate and wash buffer by aspiration. Complete removal of the wash buffer is important to lower the background and improve the effectiveness of the immunoassay. After completion of the formation and purification of the immune complexes, the resulting immunoprecipitated proteins can be further analyzed. Frequently, this next step is the separation of proteins by SDS-PAGE.

A major disadvantage of affinity based molecular pull down and immunoprecipitation procedures as commonly practiced is that the affinity matrix is difficult to visualize in the tubes used in the complex formation and purification steps. This difficulty in visualization leads to inefficient manipulations and results in loss of material and quantitative variability of results. For example, agarose or polyacrylamide beads generally are non-colored, i.e., translucent or white, and are difficult to visualize in the tubes, which makes procedural manipulations tedious. Due to this poor visibility, the beads can be lost during the aspiration of the lysate supernatant in the process of removal of the unbound proteins. Additionally, there can be accidental removal of the agarose or polyacrylamide beads from the tubes during the washing and aspiration steps due to the poor visibility of the beads. The difficulties and inaccuracies caused by the poor visibility of the beads are major limitations of the affinity based molecular pull down and immunoprecipitation experiments. Thus, a substantial need remains for an adaptation that would improve the visibility of the affinity matrix without altering its functioning in the molecular pull down or immunoprecipitation procedure. Such an adaptation would make the handling of the affinity matrix much easier for the individual conducting the molecular pull down or immunoprecipitation procedure. Improved handling would result in improved efficiency in manipulations and reduce the loss of material and quantitative variability of results. In short, such an adaptation would improve the efficiency and reliability of affinity based molecular pull down and immunoprecipitation procedures.

The affinity of certain dyes for proteins has been known and utilized for some time in various applications. Dyes have long been utilized as affinity ligands for the purification of proteins in affinity chromatography. Affinity chromatography is a procedure which separates a substance from a mixture by virtue of the biospecific recognition and affinity (involving noncovalent interactions) of that substance for a ligand immobilized to a support. The dyes that have been employed to purify proteins were originally developed for use in the textile industry. These dyes include triazine dyes that are based on the chemistry of cyanuric chloride (1,3,5-trichlorotriazine). Triazine dyes have been used as ligands for affinity chromatography because they offer advantages in both preparation and use over more conventional immobilized coenzyme and various other biological group-specific media. These advantages include a protein binding capacity that can be significantly higher than that of natural biospecific media, low cost, general availability and ease of preparation. See, for example, Christopher R. Lowe and James C. Pearson, *Affinity Chromatography on Immobilized Dyes*, Methods In Enzymology, Vol. 104, 97-113 (1984).

U.S. Pat. No. 5,597,485 discloses a process for separating proteins using a polymeric composition that includes a polymer formed from at least one monomer containing a polymerizable moiety chemically bonded to a synthetic anionic organic dye. The dye has an affinity for the protein to be separated. The process for separating proteins includes retaining the protein on the dye fraction and then recovering the protein from the polymer. The process is applicable to affinity chromatography but is not limited to chromatographic columns. The process includes contacting the polymer with the solution containing the protein to be separated and separating the colored particles from the solution by means of filtration, centrifugation, or similar means. The process, however, deliberately utilizes dyes possessing a specific affinity for the protein to be separated and the protein is isolated and purified by binding specifically to this dye.

U.S. Pat. No. 4,546,161 discloses a process of producing affinity chromatography media by reacting mono or di-chloro triazine dyes with a solid support matrix possessing free hydroxy or amino groups. The solid support matrix is a polymer or copolymer of agarose, dextrose, dextran or acrylamide. The dyes are reacted in the presence of an alkali metal hydroxide and an alkali metal salt. The dyes are linked to the solid support matrix via the triazine ring, providing high and specific protein-binding capacity. The media are designed specifically for use in affinity chromatography for the efficient and highly specific isolation and purification of proteins using triazine dyes selected to specifically bind the proteins of interest.

Similarly, U.S. Pat. No. 4,880,915 discloses a process for purifying a specific protein, human TNF, comprising applying a solution containing human TNF to a column packed with a dye-bonded crosslinked agarose gel, eluting the column to release the bound human TNF, and recovering a column fraction of purified human TNF. The crosslinked agarose gel comprises a crosslinked agarose gel support to which a dye ligand is covalently bonded. The dye ligand is either Cibacron Blue F3GA, Procion Red HE3B or Green A and the human TNF is retained by specifically interacting with the dye ligand.

Dyes have also been employed for their ability to enhance the visibility of a substance in the specific application of nucleic acid precipitation. WO 97/12994 discloses a method for precipitating soluble nucleic acid from a solution by adding a polymeric carrier molecule that is coupled to an indicator molecule. The technique of nucleic acid precipitation is often prone to unpredictable failure due to loss of precipitated nucleic acid pellets during the removal of supernatant phases, due to the lack of visibility of the nucleic acid pellets. The nucleic acids are precipitated by adding a sufficient amount of salt and alcohol to the aqueous solution to cause the nucleic acids to precipitate out of solution. Alcohol and salt are common ingredients for the technique of nucleic acid precipitation, and ethanol is the alcohol most commonly used in the procedure.

The modified carrier molecule disclosed in WO 97/12994 has the same solubility and precipitation properties as the unmodified molecule and co-precipitates with the nucleic acid, but is readily visualized and enables the user to observe the location of nucleic acid in the treated sample. The solubility and precipitation properties of both the unmodified and modified molecule are specific to the precipitation and centrifugation techniques generally employed in nucleic acid precipitation. Specifically, nucleic acids are soluble in more aqueous solutions and aggregate when the dielectric constant of the aqueous solutions is lowered, such as by adding alcohol to the aqueous solution. The aggregation causes the nucleic acids to collectively possess sufficient mass to precipitate out of the aqueous solution. The precipitate has to be separated from the aqueous solution by subjecting the solution to high speed centrifugation of around 5000 g for a period of time of around five minutes. Thus, the modified carrier molecule would not be employable in alternative experiments, and there is no suggestion in WO 97/12994 that the modified carrier molecule would be applicable to alternative techniques. Rather, the method and carrier molecule are limited specifically to nucleic acid precipitation techniques.

SUMMARY OF THE INVENTION

Among the objects of the invention is the provision of an affinity matrix, having relatively low non-specific protein binding capability that can be more readily monitored during an affinity based molecular pull down experiments to avoid the inadvertent loss of affinity matrix during the separation and thereby improve quantitative recovery of affinity complexes.

Briefly, therefore, the present invention is directed to an affinity matrix for the isolation of a molecule from an aqueous solution. The affinity matrix comprises a polymeric support, a dye attached to a fraction of the polymeric support to enable optical detection of the polymeric support, and an affinity ligand other than the dye attached to a fraction of the polymeric support for the capture of a molecule.

The present invention is further directed to a method for the isolation of a biomolecule from an aqueous solution. The method comprises combining the aqueous solution with an affinity matrix comprising a polymeric support and separating the affinity matrix from the aqueous solution. A dye is attached to a fraction of the polymeric support which enables optical detection and monitoring of the affinity matrix and, accordingly, reduces the likelihood of the loss of affinity matrix during the separation step. In addition, an affinity ligand other than the dye is also attached to a fraction of the polymeric support for the capture of the biomolecule.

Other objects will be in part apparent and in part pointed out hereinafter.

DETAILED DESCRIPTION OF THE INVENTION

As used herein "colored polymer" or "colored polymeric support" refers to polymeric materials to which dyes have been attached. These dyes are preferably dyes which are inherently low protein binding dyes or are which have been modified to be low protein binding. "Non-colored polymer" or "non-colored polymeric support" refers to polymeric supports, such as cross-linked agarose, to which dyes have not been attached. "Colored polymer" or "colored polymeric support" refers to a polymeric support to which a dye has been attached. A "colored affinity matrix" is an affinity matrix which contains a colored polymeric support.

In one embodiment, the affinity matrix of the present invention comprises a particulate polymeric material to which dye and an affinity ligand for a biomolecule or other molecule of interest are attached. In general, the affinity matrix may comprise (i) particulate polymeric material to which dye but not affinity ligand is attached, (ii) particulate polymeric material to which affinity ligand but not dye is attached, or (ii) particulate material to which both dye and affinity ligand are attached, provided a dye is attached to a fraction of the particulate material and affinity ligand is attached to a fraction of the particulate material. Thus, for example, the affinity matrix may comprise (i) a mixture of particulate materials wherein some of the particles in the mixture contain dye and other particles contain affinity ligand but none of the particles contain both dye and affinity ligand, (ii) a mixture of particulate materials wherein some of the particles in the mixture contain both dye and affinity ligand and other particles contain dye or affinity ligand but not both, or (iii) a substantially homogenous particulate material wherein substantially all of the particles contain both dye and affinity ligand (in this embodiment, the fraction of the affinity matrix particulate material to which dye is attached is 1 and the fraction of the affinity matrix particulate material to which affinity ligand is attached is also 1).

Preferably, the dye and affinity ligands are attached to separate fractions of the particulate polymeric material. For example, the dye may be attached from about 1% to about 50% by weight of the particulate polymeric material comprising the affinity matrix and the affinity ligand is attached to the balance of the particulate polymeric material defining the affinity matrix, i.e, about 50% to about 99% by weight of the particulate polymeric material comprising the affinity matrix. More preferably, the dye is bound to about 1% to about 15% by weight of the particulate polymeric material comprising the affinity matrix and the affinity ligand is attached to the remainder of the balance of the particulate polymeric material comprising the affinity matrix, i.e, about 85% to about 99% by weight of the particulate polymeric material comprising the affinity matrix. Still more preferably, the dye is bound to about 2% to about 10% by weight of the particulate polymeric material comprising the affinity matrix and the affinity ligand is attached to the remainder of the balance of the particulate polymeric material comprising the affinity matrix, i.e, about 90% to about 98% by weight of the particulate polymeric material comprising the affinity matrix. In general, the relative proportions of the two fractions depends upon the color intensity (determined optically or visually) of the dye and its capacity when bound to the particulate material for non-specific protein binding; for example, dyes which provide the particulate material to which they are bound with a greater capacity for non-specific protein binding are preferably used in lower proportion than are dyes which provide the particulate material to which they are bound with lesser capacity for non-specific protein binding.

The dyes employed in the invention are preferably dyes that have a relatively low protein binding capability when attached to a polymeric support. In general, these dyes are covalently coupled to a polymeric support; accordingly, the dyes preferably either possess a reactive group or are capable of being modified to provide a reactive group to enable covalent coupling to a polymeric support. Examples of reactive groups include, but are not limited to mono- and dichloro triazines, vinyl sulfone groups, monochloro difluoro pyrimidimium, β-sulfatoethylsulfone, and isothiocyanate. Azo, anthroquinone and phthalocyanine are the three main types of chromophores that predominate in the ranges of reactive dyes. The dyes employed in the invention can provide the polymeric support with any color, provided that when the dye is attached to the polymer an affinity matrix comprising polymeric support to which the dye has been attached is optically detectable and preferably readily visible to the naked eye in ambient light.

Suitable dyes also include those dyes that go beyond the scope of colorimetric dyes that are visible by the naked eye such as fluorescent dyes that require excitation by an appropriate wavelength of light for visualization. The fluorescent dyes provide for a much higher sensitivity to detection, which may be important when working with very small amounts of affinity matrix. An example would be a fluorescent affinity matrix used in a molecular pull-down experiment in preparation for mass spectrometry (MALDI) analysis. The affinity matrix sample may be applied directly to the MALDI target slide at a few microliters per application. The presence of the affinity matrix sample on the MALDI target could be determined visually by fluorescence upon exposure to a suitable wavelength of light.

Fluorescent molecules emit photons from excited electronic states and are characterized by absorption/excitation and emission spectra. The fluorescent dyes may be short-lived or long-lived in fluorescent emission and are further characterized by Stokes shift, and quantum yield. Fluorescein isothiocyanate represents a commonly used reactive fluorescent marker that is short-lived in emission, possesses a relatively narrow Stokes shift, and has a relatively high quantum yield. Rhodamine is another commonly used fluorescent dye, which emits at a longer wavelength than fluorescein. Lanthanide metal chelates represent a class of fluorescent compounds which possess a relatively large Stokes shift and are long-lived in fluorescent emission. This important class of fluorescent molecules generally require another strongly absorbing molecule to transfer the light energy to induce the strong fluorescence. Examples of lanthanide metals are terbium and europium which are commonly chelated by a polydentate chelate. Other examples of fluorescent compounds include napthalenes, pyrenes, coumarin derivatives, pyridyloxazole derivatives, and ruthenium complexes.

In general, the dye attached to the polymeric support may be one (or more) which intrinsically has (have) a low protein binding capability or it may be one (or more) which has (have) been modified to have a low protein binding capability when attached to a polymeric support, or combinations thereof. Preferably, the affinity matrix comprises a dye which intrinsically has a low protein binding capability. In either event, the dye(s) selected preferably do not significantly increase non-specific protein binding by the affinity matrix; otherwise, the benefits of enhanced optical detection and monitoring of the affinity matrix is more than offset by non-specific protein binding during the molecular pull down or immunoprecipitation procedure. For example, the capacity of the affinity matrix, on a weight basis, for non-specific binding of protein present in a lysate of a naturally-occurring mammalian cell under physiological salt and pH conditions is less than 100 times the capacity of a reference matrix under the same conditions wherein the reference matrix is substantially identical to the affinity matrix except that the no dye is bound to any of the particulate material of the reference matrix. Preferably, the capacity of the affinity matrix, on a weight basis, for non-specific binding of protein present in a lysate of a naturally-occurring mammalian cell under physiological salt and pH conditions is less than 50 times the capacity of the reference matrix under the same conditions. More preferably, the capacity of the affinity matrix, on a weight basis, for non-specific binding of protein present in a lysate of a naturally-occurring mammalian cell under physiological salt and pH conditions is less than 10 times the capacity of the reference matrix under the same conditions. Still more preferably, the capacity of the affinity matrix, on a weight basis, for non-specific binding of protein present in a lysate of a naturally-occurring mammalian cell under physiological salt and pH conditions is less than 3 times the capacity of a reference matrix under the same conditions.

Low protein binding dyes preferably are selected from dyes possessing azo chromophores, anthroquinone chromophores, and phthalocyanine chromophores. More preferably, representative dyes intrinsically possessing low protein binding capability when attached to a polymeric support may be selected from the Remazol family of dyes, dyes possessing a vinyl sulfone, the Procion family of dyes, dyes possessing a mono or dichloro triazine, and the Drimarene family of dyes, dyes possessing a monochloro difluoro pyrimidimium ring. Examples of suitable low protein binding dyes, include, but are not limited to 5-[(4,6-dichloro-1,3,5-triazin-2-yl)amino]-4-hydroxy-3-(phenylazo)-2,7-Naphthalenedisulfonic acid, disodium salt (Procion Red MX-5B); Procion Blue MX-R; Remazol Violet R-4B; Procion Red MX-BRA; 5-(acetylamino)-4-hydroxy-3-[[2-hydroxy-4-[[2-(sulfooxy)ethyl]sulfonyl]phenyl]azo]-2,7-Naphthalenedisulfonic acid, copper complex (Remazol Brilliant Violet 5R); Procion Red MX-GBA; Blue MX-4RD (Navy Blue 21); Blue MX-2G (Cobalt Blue 22); Dharma Fire Red 10; 6-(acetylamino)-4-hydroxy-3-[[3-[[2-(sulfooxy)ethyl]sulfonyl]phenyl]azo]-2-Naphthalenesulfonic acid, disodium salt (Remazol Brilliant Orange 3R, Reactive Orange 16); Remazol Brilliant Red BB (Reactive Red 21); Procion Turquoise H-A; Remazol Brilliant Scarlet R-3G; Remazol Brilliant Orange R-FN; and Reactive Blue 21. Preferred low protein binding dyes for use in the invention include, but are not limited to, 6-(acetylamino)-4-hydroxy-3-[[3-[[2-(sulfooxy)ethyl]sulfonyl]phenyl]azo]-2-Naphthalenesulfonic acid, disodium salt (Remazol Brilliant Orange 3R, Reactive Orange 16), Remazol Brilliant Red BB (Reactive Red 21), Procion Turquoise H-A, Remazol Brilliant Scarlet R-3G, Remazol Brilliant Orange R-FN, Remazol Violet R-4B, 5-(acetylamino)-4-hydroxy-3-[[2-hydroxy-4-[[2-(sulfooxy)ethyl]sulfonyl]phenyl]azo]-2,7-Naphthalenedisulfonic acid, copper complex (Remazol Brilliant Violet 5R), and Reactive Blue 21. More preferred low protein binding dyes include, but are not limited to 6-(acetylamino)-4-hydroxy-3-[[3-[[2-(sulfooxy)ethyl]sulfonyl]phenyl]azo]-2-Naphthalenesulfonic acid, disodium salt (Remazol Brilliant Orange 3R, Reactive Orange 16), Remazol Brilliant Red BB (Reactive Red 21), Remazol Brilliant Scarlet R-3G, Remazol Brilliant Orange R-FN, and Reactive Blue 21. Still more preferred low protein binding dyes include, but are not limited to Remazol Brilliant Red BB (Reactive Red 21) and 6-(acetylamino)-4-hydroxy-3-[[3-[[2-(sulfooxy)ethyl]sulfonyl]phenyl]azo]-2-Naphthalenesulfonic acid, disodium salt (Remazol Brilliant Orange 3R, Reactive Orange 16).

Low protein binding may also be achieved by modifying a dye so that it has a low protein binding capability. These dyes may also be selected generally from dyes possessing Azo chromophores, anthroquinone chromophores, and phthalocyanine chromophores. Dyes may also be used that are not in the visible spectrum, such as fluorescent dyes and dyes that are visible in the UV spectrum or the IR spectrum. Preferably, the dyes may be selected from the Remazol family of dyes, dyes possessing a vinyl sulfone reactive group, the Procion family of dyes, dyes possessing a mono or dichloro triazine group, and the Drimarene family of dyes, dyes possessing a monochloro difluoro pyrimidimium ring. Examples of protein binding dyes include, but are not limited to Reactive Brown 10, and Reactive Red 120. The modifications that can make a dye low protein binding can include gelatin absorption and crosslinking. The gelatin absorption and cross-linking physically blocks the sites at which the protein binding dye binds protein. Therefore, less proteins are bound by the dye because the sites at which they bind to the protein are blocked by the gelatin. The gelatin acts to block the actual protein binding sites of the protein binding dye that is attached to the polymeric support and the cross-linking acts to lock the blocking gelatin onto the polymeric support. The gelatin absorption and cross-linking can be accomplished by saturating the colored polymeric support in a gelatin in water preparation and then cross-linking with an appropriate reagent, such as 1-ethyl-3-(3-dimethylaminopropyl) carbodiimide hydrochloride. This procedure was employed to attach gelatin to a beaded agarose matrix with covalently attached Reactive Red 120. Appropriate modifications to this procedure and the selection of different procedures altogether could be made by one of ordinary skill in the art, who is familiar with modifications to block protein binding and the procedures with which they are accomplished.

The amount of dye that can be attached to the polymeric support can vary considerably, depending on the objectives of the particular affinity based molecular pull down or immunoprecipitation experiment. Upper limits of the amount of dye that can be attached to the polymeric support are those amounts that would alter or compromise the functioning of the polymeric support. Lower limits are set by the amount of dye that enable the polymeric support to be optically or visibly detected, for example, by visibility in ambient light. Other pertinent considerations in choosing the amount of dye to attach to the polymeric support include the capacity of the colored polymeric support to be further modified with affinity ligands. Evaluating these variables and choosing an appropriate amount of dye to attach to the polymeric support to meet the objectives of a particular molecular pull down or immunoprecipitation experiment is well within the skill of an ordinary practitioner in the art.

Generally, however, the amount of dye that can be attached to the polymeric support is between about 0.5 micromole of dye/$cm_3$ of polymeric support to about 20 micromoles of dye/$cm^3$ of polymeric support. Preferably, the amount of dye that is attached to the polymeric support is between about 1 micromole of dye/$cm^3$ of polymeric support to about 6 micromoles of dye/$cm^3$ of polymeric support. More preferably, the amount of dye that is attached to the polymeric support is between about 2 micromoles of dye/$cm^3$ of polymeric support to about 4 micromoles of dye/$cm^3$ of polymeric support.

The polymeric support is generally any polymer capable of being used as an affinity matrix in affinity based molecular pull down or immunoprecipitation experiments which includes an attachment site to enable the attachment of a dye. The polymer preferably exhibits low non-specific protein binding and high binding capacity for both the dye and any affinity ligands or protein binding ligands with which it may be modified. The polymers can be natural or synthetic. The natural or synthetic polymers may be cross-linked. Such polymers include but are not limited to natural agarose, cross-linked agarose, dextran, cross-linked dextran, xylan alginate, chitosan, beaded cellulose, polyacrylamide, polyacrylate, polystyrene, polymethacrylate, polycaprolactones, polyoxyethylenes, polyvinyl resins, agarose-polyacrylamide copolymers, and dextran-polyacrylamide copolymers. Combinations of these and other polymers are also included within the scope of the invention, provided that the combined polymers possess the desired characteristics of low non-specific protein binding and high binding capacity for both dyes and affinity ligands. Preferred polymers include those frequently employed in affinity based molecular pull down and immunoprecipitation experiments. Thus, natural agarose, cross-linked agarose, polyacrylamide, and cross-linked dextran are the preferred polymers for use in the invention. Cross-linked agarose is the more preferred polymer for use in the invention. The polymeric support can take any form appropriate for the affinity based molecular pull down or immunoprecipitation application for which they are intended. The polymeric support can be soluble or insoluble in aqueous solutions. Preferably, the polymeric support is insoluble in aqueous solutions. For most affinity based molecular pull down or immunopecipitation applications the polymeric supports will be in the form of particles or beads. Thus, it is preferred that the polymeric support be in the form of particles or beads.

In general, the affinity matrix will comprise a particulate polymeric support in which the particles have an average size of less than about 1,000 micrometers. Typically, the particles in the particulate polymeric support will have an average size of less than about 700 microns, more typically less than 600 microns. For example, for some applications the particles of the particulate polymeric support will have an average size less than about 400 microns and in other applications the particles will have an average size less than about 200 microns.

The particles of natural and cross-linked agarose typically range from about 20 to about 300 micrometers in diameter. Preferably, the particles of natural and cross-linked agarose range from about 30 to about 250 micrometers in diameter. More preferably, the particles of natural and cross-linked agarose range from about 40 to about 165 micrometers in diameter. The particles of polyacrylamide typically range from about 20 to about 200 micrometers in diameter. Preferably, the particles of polyacrylamide range from about 30 to about 150 micrometers in diameter. More preferably, the particles of polyacrylamide range from about 40 to about 105 micrometers in diameter. The particles of dextran and cross-linked dextran typically range from about 15 to about 600 micrometers in diameter. Preferably, the particles of dextran and cross-linked dextran range from about 20 to about 400 micrometers in diameter. More preferably, the particles of dextran and cross-linked dextran range from about 50 to about 300 micrometers in diameter.

Thus, an example of a suitable colored polymeric support for use in the invention would be natural agarose particles ranging from about 30 to about 250 micrometers in diameter possessing between about 0.5 to about 20 micromoles of dye per $cm^3$ of natural agarose. Another example of a suitable colored polymeric support for use in the invention would be polyacrylamide particles ranging from about 30 to about 150 micrometers in diameter and possessing between about 0.5 to about 20 micromoles of dye per $cm^3$ of polyacrylamide. A further example of a suitable colored polymeric support for use in the invention would be cross-linked dextran particles ranging from about 20 to about 400 micrometers in diameter and possessing between about 0.5 to about 20 micromoles of dye per $cm^3$ of cross-linked dextran.

A preferred colored polymeric support for use in the invention is cross-linked agarose particles ranging from about 20 to about 300 micrometers in diameter possessing between about 1 to about 6 micromoles of dye per $cm^3$ of cross-linked agarose. Another preferred colored polymeric support for use in the invention is cross-linked agarose particles ranging from about 20 to about 300 micrometers in diameter possessing between about 2 to about 4 micromoles of dye per $cm^3$ of cross-linked agarose.

A more preferred colored polymeric support for use in the invention is cross-linked agarose particles ranging from about 30 to about 250 micrometers in diameter possessing between about 1 to about 6 micromoles of dye per $cm^3$ of cross-linked agarose. Another more preferred colored polymeric support for use in the invention is cross-linked agarose particles ranging from about 30 to about 250 micrometers in diameter possessing between about 2 to about 4 micromoles of dye per $cm^3$ of cross-linked agarose.

An even further preferred colored polymeric support for use in the invention is cross-linked agarose particles ranging from about 40 to about 165 micrometers in diameter possessing between about 1 to about 6 micromoles of dye per $cm^3$ of cross-linked agarose. Another even further preferred colored polymeric support for use in the invention is cross-linked agarose particles ranging from about 40 to about 165 micrometers in diameter possessing between about 2 to about 4 micromoles of dye per $cm^3$ of cross-linked agarose. The dye may be covalently attached to the polymeric support by any suitable means available to those skilled in the art. The attachment preferably occurs via reactive groups on the dye and attachment sites on the polymeric support. Attachment sites on the polymeric support include, but are not limited to hydroxyl groups, amine groups, and carboxyl groups. It is possible to create additional attachment sites by converting some or all of the naturally occurring attachment sites on the polymer to different attachment sites. For example, hydroxyl groups found on a given polymeric support can be converted to functional groups such as amines, sulfhydryl groups or carboxylic acids. Likewise, it is also possible to create additional reactive groups on the dye by converting some or all of the naturally occurring reactive groups on the dye to different reactive groups. The dye could be modified to contain an amine group, for example.

The dye may be covalently coupled, for example, by the substitution of chlorine atom(s) in the triazine ring of certain of the dyes with the hydroxyl groups on certain of the polymer matrices. The dyes may also be attached via the vinyl sulfone groups of certain of the dyes and hydroxyl groups of some of the polymers. Preferably, the dye is directly covalently attached to the polymeric support. However, it is also possible, although not preferred, for the dye to be indirectly covalently attached to the polymeric support. Such an indirect attachment could involve the use of a spacer or different molecule to attach the dye to the polymeric support. Typical spacers include hydrocarbon spacers such as hexyl spacers.

In one embodiment, dyes are attached to an agarose resin by any means known in the art. For example, the agarose may be centrifuged, washed repeatedly, and suspended in sodium bicarbonate. The dye may then be dissolved in sodium chloride and the salt/dye solution is added to the resin carbonate slurry. The combined salt/dye solution and resin/carbonate slurry may then be incubated (e.g., at temperatures between 25° C. and 80° C.) for a period of time ranging from one hour to several hours and then centrifuged or filtered to remove the supernatant. The colored agarose pellet is washed repeatedly with water until unbound dye is removed. The resin is resuspended in a suitable storage buffer.

Dyes can also be attached to the agarose utilizing a similar procedure employing alkaline conditions at temperatures between 25° C. and 80° C. for a period of time ranging from one hour to several hours. The alkaline conditions can be provided by utilizing NaOH in the procedure. After coupling, the polymer is washed repeatedly with water to remove unbound dye. This procedure has been employed to attach certain Procion and Remazol dyes to agarose (Hasnaoui, M., et al., J. Chromatogr. A, 766, 49-60, 1997). It is understood that when different dyes and other polymers are coupled, appropriate variations and adjustments in the attachment procedures may need to be made which will be obvious to those of skill in the art.

After the dye is attached, the colored polymeric support preferably possesses similar solubility and centrifugation characteristics and similar density as possessed by the same polymer to which no dye is bound. For example, if the polymer is insoluble in aqueous solution, the colored polymeric support is also preferably insoluble in aqueous solution. Preferably, the colored polymer can be easily collected from aqueous solutions by centrifugation of less than 700×g.

Another embodiment of the invention is directed to a method for the isolation of a biomolecule from an aqueous sample solution using the affinity matrix of the invention, the affinity matrix being characterized in that it has improved visibility and possesses low non-specific protein binding characteristics. The affinity matrix used in the method of isolating a biomolecule of interest may comprise a colored polymeric support modified with affinity ligands or it may comprise a mixture of a colored polymeric support and a non-colored affinity matrix.

A colored polymeric support can be modified with the affinity ligands appropriate for the particular affinity based molecular pull down application or immunoprecipitation application. Examples of frequently used affinity ligands include antibodies, metal chelates, glutathione, streptavidin, monomeric streptavidin, molecules with the binding properties of streptavidin such as modified forms of streptavidin, avidin, monomeric avidin, molecules with the binding properties of avidin such as modified forms of avidin, streptactin, monomeric streptactin, molecules with the binding properties of streptactin such as modified forms of streptactin, extravidin, monomeric extravidin, molecules with the binding properties of extravidin such as modified forms of extravidin, neutravidin, monomeric neutravidin, molecules with the binding properties of neutravidin such as modified forms of neutravidin, protein A, a molecule with the binding properties of protein A such as fragments, combinations, recombinant forms or other variants of protein A, protein L, a molecule with the binding properties of protein L such as fragments, combinations, recombinant forms or other variants of protein L, protein G, a molecule with the binding properties of protein G such as fragments, combinations, recombinant forms, or other variants of protein G, protein A/G, a molecule with the binding properties of protein A/G such as fragments, combinations, recombinant forms, or other variants of protein A/G, protein L/A, a molecule with the binding properties of protein L/A such as fragments, combinations, recombinant forms or other variants of protein L/A, calmodulin, a molecule with the binding properties of calmodulin, biotin, and a molecule with the binding properties of biotin.

As modified with an affinity ligand, the affinity matrix is suitable for use with all types of affinity based molecular pull down or immunoprecipitation procedures because the affinity matrix has similar centrifugation and solubility characteristics as does a comparable non-colored affinity matrix and does not function differently in isolating, purifying, and analyzing biomolecules of interest. The methods by which the colored polymeric support can be modified with affinity ligands are well known to those skilled in the art.

No particular adjustments to the standard affinity based molecular pull down methods are necessary because the affinity matrix of the invention has similar centrifugation and solubility characteristics to an equivalent non-colored affinity matrix and does not function any differently in isolating and purifying biomolecules of interest. The procedures for affinity based molecular pull down experiments (affinity capture) will vary, however, depending on the nature of the affinity ligand affixed to the matrix and its target biomolecule. A person of ordinary skill in the art is well acquainted with the various procedures for affinity based molecular pull down experiments. Affinity based molecular pull down procedures have the following basic steps. The affinity matrix possessing attached affinity ligands is incubated with an aqueous solution containing the biomolecule of interest. The nature of the affinity interaction, including the strength and duration of the interaction, can vary widely, depending on the objectives the particular experiment or procedure. Thus, the affinity interaction between the affinity ligand and the biomolecule of interest can be transient or of sufficient duration that a specific complex forms between the affinity ligand and the biomolecule of interest. In those experiments and procedures in which a complex forms, the affinity matrix to which the complex is attached is separated from the aqueous solution by centrifugation. Unbound proteins are then removed by aspirating the supernatant and washing the complex. The particles can be washed by rinsing with a solution such as lysis buffer and removing the lysate and wash buffer by aspiration. Filtration may also be employed to separate the complex from the aqueous solution. The biomolecule of interest can then be removed from the complex or can be analyzed for activity while still part of the complex that is attached to the affinity matrix. If removed from the complex, the biomolecule could be subjected to physical, chemical, or functional analysis. For example, the molecular weight of the biomolecule could then be determined by SDS/PAGE or an enzymatic assay could be conducted on the unbound biomolecule.

Immunoprecipitation is one type of affinity based molecular pull down procedure. The basic procedure of immunoprecipitation involves preparation of the antigen solution and forming and purifying the antibody-antigen complexes. The antibody-antigen complexes are formed by the addition of specific antibodies to the lysate. The affinity of antibodies for their respective antigens will cause the antibody-antigen complexes to form rapidly. An affinity bead suspension, such as a protein A or protein G bead suspension, is then added to the aqueous solution containing the antibody-antigen complexes to purify the complexes. The high affinity possessed by protein A and protein G for the Fc portion of the antibody facilitates the purification of the complexes. After the complex is bound to the particles of the polymeric support through the protein A/G-antibody interaction, the particles are separated from the aqueous solution by centrifugation. Unbound proteins are then removed by aspirating the supernatant and washing the complex. The washes are removed by aspiration. Filtration may also be employed to separate the particles of the affinity matrix from the aqueous solution. The biomolecule of interest can then be removed from the complex or can be analyzed for activity while still part of the complex that is attached to the polymeric support. Harlow, supra, incorporated herein by reference, describes the suitable conditions for immunoprecipitation experiments. No particular adjustments to the standard immunoprecipitation methods are necessary because the colored affinity matrix has similar centrifugation and solubility characteristics as a non-colored affinity matrix of the same polymer and does not function any differently in isolating and purifying biomolecules of interest. However, in contrast to non-colored affinity matrices, the colored affinity matrix will be visible during the various manipulations of the immunoprecipitation procedure.

Since there are no modifications to the procedures of affinity based molecular pull down and immunoprecipitation due to the presence of the colored affinity matrix, the following general steps are followed in both procedures. The first step of the affinity based molecular pull down method of purifying and isolating a biomolecule of interest involves combining an aqueous solution containing the biomolecule of interest with a colored affinity matrix having improved visibility and low non-specific protein binding characteristics. The combining can be accomplished by adding the colored affinity matrix to the aqueous solution containing the biomolecule. Preferably, the combining is accomplished by adding the aqueous solution containing the biomolecule to the colored affinity matrix.

The aqueous solution containing the biomolecule of interest is typically a lysate, lysate fractions, or buffered solution containing proteins or other biomolecules or modified biomolecules in a purified or unpurified form, although other aqueous solutions containing biomolecules can be used. Biomolecules can be naturally occurring, of synthetic origin or naturally occurring or synthetic biomolecules that have been modified in some way. Examples of naturally occurring biomolecules of interest include, but are not limited to, peptides, polypeptides, individual proteins, glycoproteins, enzymes, nucleotides, polynucleotides, nucleic acid polymers such as DNA or RNA, carbohydrates, lipids, or complexes containing proteins. Examples of synthetic biomolecules include, but are not limited to, synthetic peptides, synthetic polypeptides, synthetic individual proteins, synthetic glycoproteins, synthetic nucleotides, synthetic polynucleotides, synthetic nucleic acid polymers such as DNA or RNA, synthetic enzymes, synthetic carbohydrates, synthetic lipids, or synthetic complexes containing proteins. Examples of modified biomolecules include, but are not limited to, naturally occurring or synthetic biomolecules that have been modified by procedures such as enzymatic cleavage or provided with synthetic tags such as biotinylation or amino acid epitope tags. The solution may also contain mixtures of these biomolecules.

The second step of the method involves separating the colored affinity matrix from the aqueous solution. The colored affinity matrix is typically separated from the aqueous solution by centrifugation and aspiration of the supernatant. However, filtration or another suitable method could be employed to separate the matrix from the aqueous solution, depending on the particular experiment. Centrifugation is typically conducted at 8,000×g for 30 seconds or less. However, there can be considerable variation in suitable centrifugation procedures for immunoprecipitation and affinity based molecule pull down experiments. Thus, a slower speed centrifugation could be employed for a longer period of time. Similarly, a higher speed centrifugation could be employed for a shorter period of time, depending on the type of immunoprecipitation and affinity based molecular pull down experiment and the preference of the operator.

The unbound biomolecules can be removed from the colored affinity matrix by washing the colored affinity matrix. The washes are removed by aspiration. Due to its optical detectability, the colored affinity matrix can be optically monitored during the process of washing and aspirating. Preferably, the optical monitoring is done by operator visualization in ambient light. However, the optical monitoring could also be done by machine or device and could even be automated. Thus, the operator is able to visually confirm the location of the colored affinity matrix during the washing process and is less likely to accidentally remove the particles of the colored affinity matrix by aspiration. This ability to optically monitor the matrix will increase the reliability and reduce the quantitative variability of the method.

Depending on the objectives of the experiment, a successful experiment may have the biomolecule of interest bound to the colored affinity matrix through affinity interactions. An additional step of the method of purifying and isolating a biomolecule of interest would be to release or treat the bound biomolecules to allow subsequent physical, chemical, or functional analysis. Examples of physical analysis include molecular weight determination by SDS/PAGE. Biochemical analysis could include identifying post-translational modifications, and functional analysis could include an enzymatic assay, for example.

The colored affinity matrix used in the affinity based molecular pull down method of purifying and isolating a biomolecule of interest may comprise the colored polymeric support of the invention modified with affinity ligands or it may comprise a mixture of a colored polymeric support of the invention and a non-colored affinity matrix. This mixture is prepared by combining the colored polymeric support with a non-colored affinity matrix.

The density, solubility and centrifugation properties of the colored polymeric support and the non-colored affinity matrix should be such that the colored affinity matrix exhibits improved optical detectability relative to conventional non-colored affinity matrices. Preferably, the colored polymeric support of the invention has substantially similar centrifugation and solubility properties and the same approximate density as the non-colored affinity matrix with which it is being combined. When they have similar properties and density, the colored polymeric support will tend to distribute substantially uniformly in the non-colored affinity matrix to provide a uniform color, which in one embodiment may be visualized in ambient light by an operator or by optically by an optical detection device. By uniform distribution is meant that the colored polymeric support is evenly distributed within the non-colored affinity matrix after mixing so that the appearance of the colored affinity matrix has an even and uniform color with no concentration of color in any particular area of the matrix. This distribution of the colored polymeric support within the non-colored affinity matrix remains uniform after centrifugation. Furthermore, the colored polymeric support does not alter or compromise the functioning of the non-colored affinity matrix in isolating and purifying molecules of interest.

In general, it is preferred that the colored polymeric support and the non-colored polymeric support be prepared from the same type and size of polymer. Provided they are sufficiently similar in terms of centrifugation characteristics, solubility and density, the colored and non-colored polymeric supports may comprise different polymer types or sizes of particles. Similarly, the colored polymeric support and the non-colored polymeric support may each comprise one or more types or sizes of polymeric supports.

The affinity matrix may comprise any of a wide variety of affinity ligands on the surface of any of a wide variety of polymeric supports. For example, the affinity ligand may be any member of a binding pair of molecules (each being a member of a specific binding pair) which are naturally derived or synthetically produced. One of the pair of molecules, has an area on its surface, or a cavity which specifically binds to, and is therefore defined as complementary with a particular spatial and polar organization of the other molecule, so that the pair have the property of binding specifically to each other. Examples of types of specific binding pairs are antigen-antibody, biotin-avidin, hormone-hormone receptor, receptor-ligand, enzyme-substrate, and IgG-protein A.

In one embodiment of the present invention, the polymeric support comprises agarose and bound to the surface of the agarose is protein A ("protein A agarose") or a derivative or analog thereof having comparable binding properties to protein A agarose, protein G ("protein G agarose") or a derivative or analog thereof having comparable binding properties to protein G agarose, protein L ("protein L agarose") or a derivative or analog thereof having comparable binding properties to protein L agarose, and combinations thereof such as protein A/G agarose or agarose modified with a molecule with the binding properties of protein A/G, and protein L/A agarose or agarose modified with a molecule with the binding properties of protein L/A.

In another embodiment, bound to the polymeric support is an antibody which is specific to a peptide tag of a fusion protein, or to an epitope within a protein which may be shared among a number of proteins. Examples of the antibodies that can be attached to matrices include, but are not limited to antibodies having specificity for at least a portion of the DYKDDDDK (SEQ. ID. No. 1) amino acid sequence (e.g., anti-FLAG™ antibodies commercially available from Sigma-Aldrich), anti-polyhistidine, anti-glutathione-5-transferase, anti-myc-tag, anti-Avi-tag, anti-HA, anti-Green fluorescent protein, anti-beta galactosidase, anti-thioredoxin, anti-maltose binding protein, anti-cellulose binding domain, anti-VSV glycoprotein, and anti-luciferase.

In another embodiment, the affinity ligand bound to the polymeric support is other than a member of an antibody pair. For example, such affinity ligands include streptavidin, monomeric streptavidin, a molecule with the binding properties of streptavidin, avidin, monomeric avidin, a molecule with the binding properties of avidin, streptactin, monomeric streptactin, a molecule with the binding properties of streptactin, extravidin, monomeric extravidin, a molecule with the binding properties of extravidin, neutravidin, monomeric neutravidin, and a molecule with the binding properties of neutravidin, calmodulin, a molecule with the binding properties of calmodulin, biotin, a molecule with the binding properties of biotin, glutathione, and metal chelates.

The colored polymeric support can be combined with the non-colored affinity matrix by any suitable method. The colored polymeric support can be combined with the non-colored affinity matrix, for example, by pipetting each matrix as slurries. Thus, if it was desired to make a colored affinity matrix containing 10% of the colored polymeric support, an amount equivalent to 9 parts non-colored affinity matrix could be pipetted into a tube as a 50% slurry and then an amount equivalent to 1 part colored polymeric support could be pipetted into the same tube as a 50% slurry. The slurries could then be mixed to provide a uniform suspension. The parts could be measured either by volume or by weight. The slurries could also be filtered, weighed and then manually mixed to provide a colored affinity matrix. Thus, if it was desired to make a colored affinity matrix containing 10% of the colored polymeric support the following method could be employed. A slurry of non-colored affinity matrix and a slurry of colored polymeric support each could be filtered separately using filter paper. An amount of the colored polymeric support equivalent to 1 part by weight could be weighed and combined with an amount equivalent to 9 parts by weight of the non-colored affinity matrix obtained in the same manner. The combined colored polymeric support and non-colored affinity matrix could then be resuspended in a suitable buffer and the resulting slurry manually mixed to provide a colored affinity matrix. The selection and conducting of an appropriate method is well within the skill of a practitioner of ordinary skill in the art.

The amount of colored polymeric support in the colored affinity matrix can vary considerably and is selected according to the following three basic criteria. The colored affinity matrix is optically detectable, and exhibits comparable non-specific protein binding to that of the non-colored affinity matrix. Furthermore, the colored affinity matrix exhibits comparable specific biomolecule binding to that of a non-colored affinity matrix. Optically detectable means that the affinity matrix should be able to be detected optically either by machine or through visualization by an operator or observer. The colored affinity matrix should be able to be optically detected during the various manipulations of the procedure. Comparable non-specific protein binding means that the colored affinity matrix would not exhibit significantly more non-specific protein binding than the non-colored affinity matrix. Significantly more non-specific protein binding would be an amount that would interfere with subsequent analysis of the biomolecule target. This amount can vary depending on the specific application of the operator. Comparable specific biomolecule binding means that the colored affinity matrix will have a similar affinity and binding capacity for the biomolecule of interest in the immunoassay or molecular pull down procedure to that of a non-colored affinity matrix and binds a similar amount of this biomolecule as would a non-colored affinity matrix.

Thus, the amount of colored polymeric support in the colored affinity matrix utilized in the particular molecular pull down or immunoprecipitation experiment can range from between about 1% by volume to about 95% by volume. Preferably, the amount of colored polymeric support in the colored affinity matrix ranges from between about 2% by volume to about 50% by volume. More preferably, the amount of colored polymeric support in the colored affinity matrix ranges from between about 2% by volume to about 10% by volume. However, many variables are involved in determining the appropriate amount of colored polymeric support to be added to the non-colored affinity matrix which will be familiar to one of ordinary skill in the art. One such variable is the type of dye utilized in the colored polymeric support and the intensity of its color in ambient light. Thus a yellow dye such as Remazol Yellow GL would not have as intense a color as Remazol Brilliant Red BB, and a larger percentage of Remazol Yellow GL colored polymer may be required to achieve adequate visibility in ambient light. Another variable includes the type of molecular pull down technique; the functioning of certain affinity ligands could be more sensitive to the presence of dye molecules in the polymeric support and a smaller percentage of colored polymeric support would be able to be utilized without affecting the colored affinity matrix's affinity for the biomolecule of interest and binding of the biomolecule of interest.

The colored affinity matrix of the invention is also useful as a means of identifying a particular molecular pull down or immunoprecipitation experiment; two different molecular pull down or immunoprecipitation experiments can be distinguished by the color of the affinity matrix being employed in the experiment. Thus, the colored affinity matrix can also assist the operator of multiple experiments. Moreover, the use of a colored affinity matrix of the type herein described in an affinity based molecular pull down or immunoprecipitation experiment provides the ability to visualize and monitor the location of the affinity matrix during the procedure. This ability to visualize and monitor the location of the affinity matrix during the procedure will make the various manipulations involved in the affinity based molecular pull down or immunoprecipitation experiments much easier for the operator and will help to reduce operator error. This improvement to existing affinity based molecular pull down and immunoprecipitation techniques can greatly enhance the reliability of these powerful techniques. The following Examples are intended to illustrate but not to limit the invention.

EXAMPLE 1

Comparing the Compatibility of Different Colored and Non-Colored Matrices

Different colored and non-colored matrices were compared by mixing, followed by centrifugation and visual observation of the resulting matrix pellet.

Sepharose CL-4B agarose (non-colored) and Reactive Red 120 agarose (Sigma Product #R9129; red) were swollen and washed by standard methods to equilibrate and stored as 50% gel slurries in Tris buffered saline (TBS) containing 20% ethanol. The Reactive Red 120 agarose was added into the non-colored agarose at 0%, 5%, 10%, 25%, 50%, 100%, mixed in standard 1.5 ml microcentrifuge tubes, and centrifuged for 30 seconds in a standard microcentrifuge at 8,000× g.

The resulting pellets were carefully observed visually in ambient light for uniformity of color distribution in the matrix pellets and for over-all color intensity. All pellets showed uniform color, which was evenly distributed throughout the matrix pellet, indicating that the density and centrifugation properties of the Reactive Red 120 agarose were comparable to those of the non-colored agarose. The visual intensity of the pellets containing Reactive Red agarose varied from dark red for the 100% Reactive Red 120 agarose to light red/pink for the 5% mixture and were more visible than non-colored agarose alone. The 10% Reactive Red 120 agarose mixture was readily visible and had the desired visibility with minimal dilution of the non-colored agarose matrix (which mimics a real affinity capture agarose conjugate).

This experiment demonstrated that colored agarose mixed with non-colored agarose had the desired centrifugation properties, leading to an easily visualized, uniformly colored pellets of polymeric support after centrifugation.

EXAMPLE 2

Blocking with Proteins and Cross-Linking

We tested whether saturating the matrix beads with a known protein preparation and cross-linking that protein onto the agarose beads would shield the protein binding sites of the dye and, hence, lower the amount of non-specific lysate protein that could bind to the colored agarose matrix.

2.4 ml (1.2 ml packed gel) of Reactive Red 120 Agarose affinity resin 50% suspension (Sigma product #R0503) was dispensed into each of six tubes and centrifuged in a table top centrifuge at 2500×g for 5 minutes at room temperature. The supernatants were carefully aspirated. The resin pellets were washed by adding 9 ml water to each tube, mixing and centrifuging as above. The wash supernatants were aspirated. The pellets were washed two more times by the same procedure. Various test protein solutions were added to the pellets as indicated below:

Tube A—4 ml albumin solution at 5 mg/ml in water
Tube B—4 ml albumin solution at 20 mg/ml in 4 M NaCl
Tube C—4 ml gelatin at 20 mg/ml in water
Tube D—4 ml casein hydrolysate at 20 mg/ml in water
Tube E—4 ml gelatin hydrolysate at 40 mg/ml in water
Tube F—4 ml protein mixture (1 ml albumin solution at 5 mg/ml, 1 ml gelatin at 20 mg/ml, 1 ml casein hydrolysate at 20 mg/ml, 1 ml gelatin hydrolysate at 40 mg/ml)

Tubes were mixed and incubated at 4° C. with gentle rotational mixing for 1 hour. The tubes were then centrifuged as above to collect the resin pellets. The supernatants were removed by aspiration and the pellets were washed 3 times as above with 9 ml water per wash. After aspiration of the final wash supernatants, the pellets were each brought up to a 50% suspension (total volume per tube of 2.4 ml) by adding 1.2 ml water to each. After mixing, 0.2 ml was removed from each for subsequent analysis.

Cross-linking in 0.1 M EDAC (1-ethyl-3-(3-dimethylaminopropyl) carbodiimide hydrochloride; Sigma product #E1769) was then carried out to lock the absorbed, blocking proteins onto the resins. The pH of each resin tube was adjusted to about pH 5.4 to 5.7 with small drops of 0.1 M HCl. To each tube of suspended resin (2.2 ml per tube), 89.8 µl of an 0.47 mg/µl fresh stock solution of EDAC in water was added. The tubes were mixed and incubated at room temperature with gentle rotational mixing. The pH of was readjusted to about 5.0 to 5.7 every 30 minutes for the first two hours of the reaction. The reaction was then allowed to continue overnight (about 16 to 18 hours). To stop the reactions, the tubes were centrifuged at room temperature for 5 minutes at 2500× g. After aspirating the supernatants, the pellets were washed three times as above with 8 ml water per wash. After aspiration of the final wash supernatants, the pellets were suspended as a 50% slurry by adding 1 ml Tris buffered saline containing 20% ethanol to each and the slurries were put to 4° C. for storage. 100 µl of each 50% resin suspension (50 µl packed gel) was tested directly for the amount of non-specific background protein binding with mammalian tissue culture cell lysates as described in the following mock immunoprecipitation protocol:

Mock Immunoprecipitation Protocol

1. Make agarose bead mixtures in 1.5 ml microfuge tubes to give 50 µl packed gel per tube of 10% stained agarose mixture with non-colored agarose: Add 10 µl of stained agarose 50% slurry into 90 µl non-colored agarose 50% slurry, vortex and set on ice.

2. Wash/equilibrate agarose beads in RIPA lysis buffer (50 mM Tris-HCl, pH 8.0, 150 mM NaCl, 1% NP-40, 0.5% DOC, 0.1% SDS): Add 750 µl RIPA buffer to each tube, vortex and centrifuge in microcentrifuge for 30 seconds at 8,000×g. Aspirate supernatants carefully (or remove with a micropipet) and set tubes with bead pellets on ice. Repeat wash as above. Set final pellets on ice.

3. Thaw cell lysates (1 ml RIPA lysate of a freshly confluent tissue culture cell line from a 100 mm tissue culture plate) and set on ice. Remove denatured DNA aggregate with a pipet, if present. Transfer each lysate to a microfuge tube and centrifuge in microcentrifuge in cold room (4° C.) at 8,000×g for 10 minutes to pellet cell debris and insoluble denatured protein. Remove and combine clear supernatants to a tube on ice.

4. Mix combined lysate and added 1 ml to each washed agarose bead tube on ice. Vortex briefly and put to incubate in cold room, mixing slowly on rotating wheel, for 1 hour.

5. Centrifuge in microcentrifuge for 30 seconds at 8,000×g. Set on ice. Aspirate supernatants carefully (or remove with a micropipet) and set tubes with bead pellets on ice.

6. Wash bead pellets by adding 750 µl RIPA buffer to each tube. Vortex briefly and put to incubate in cold room, mixing slowly on rotating wheel for 5 minutes. Centrifuge in microcentrifuge in cold room (4° C.) for 30 seconds at 8,000×g. Aspirate supernatants carefully (or remove with a micropipet) and set tubes with bead pellets on ice.

7. Repeat washes two more times as in step 6.

8. Add 25 µl RIPA buffer to each tube, vortex briefly, then add 25 µl of 2X Laemmli protein gel sample buffer. Vortex briefly. Freeze samples for storage, if not used immediately.

9. Boil samples 5 minutes and centrifuge 30 seconds at 8,000×g in microfuge to pellet agarose. Run 10 μl of each supernatant and molecular weight standards onto a denaturing SDS/PAGE gel.

10. Stain with colloidal blue and/or silver stain to visualize protein bands. Photo or scan image for documentation and/or quantitation.

Results:

Tube A resin (albumin blocked)—Albumin was bound and cross-linked to the Reactive Red 120 agarose resin; non-specific lysate protein binding reduced by 70-80%.

Tube B resin (albumin in 4 M NaCl blocked)—Albumin did not bind to the Reactive Red 120 agarose resin; non-specific lysate protein binding was not reduced.

Tube C resin (gelatin blocked)—Gelatin bound well and was well cross-linked to the Reactive Red 120 agarose resin; non-specific lysate protein binding reduced by 90-98%.

Tube D resin (casein hydrolysate blocked)—Casein hydrolysate did not bind to the Reactive Red 120 agarose resin; non-specific lysate protein binding was not reduced.

Tube E resin (gelatin hydrolysate blocked)—Gelatin hydrolysate did not bind to the Reactive Red 120 agarose resin; non-specific lysate protein binding was not reduced.

Tube F resin (albumin, gelatin, casein hydrolysate, gelatin hydrolysate mixture blocked)—The mixture was partially bound and cross-linked to the Reactive Red 120 agarose resin; non-specific lysate protein binding reduced by 80-90%.

The conditions used for Tube C resin (gelatin blocked) gave optimal performance for lower non-specific lysate protein binding using this approach and could reasonably be assumed to perform adequately in immunoprecipitation and other molecular pull-down applications.

EXAMPLE 3

Non-Specific Protein Binding of Agarose Resin Conjugates with Various Dyes

Several dyes were selected from references in the scientific literature that screened dyes, potentially useful for producing affinity chromatography resins, for protein binding ability. A number of the dyes were found to be inadequate for that application, due to their poor ability to bind protein. We made agarose resin conjugates with some of these dyes and tested them for non-specific protein binding.

Procion Red MX-B5 (Aldrich Product #404365) and Remazol Brilliant Orange 3R (Aldrich Product #306509) were among dyes that had been reported to bind lysate proteins poorly (Scopes, R. K., J. Chromatogr., 376, 131-140, 1986) and to bind IgG protein poorly (Hasnaoui, M., et al., J. Chromatogr. A, 766, 49-60, 1997). Staining of agarose with these dyes was carried out by the dye immobilization procedure in Hasnaoui, M., et al., J. Chromatogr. A, 766, 49-60, 1997.

For each immobilization reaction, 2 ml of a 50% slurry of Sepharose CL-4B agarose (1 ml packed gel) was centrifuged in a table top centrifuge 5 minutes at 2500×g at room temperature, and the supernatant was removed by aspiration. The agarose resin pellets were each washed three times with 10 ml water. For each wash, the tubes were mixed after adding the water, centrifuged as above for 2.5 minutes and the supernatants were carefully removed by aspiration.

The washed agarose resin pellets were equilibrated by washing three times in 10 ml immobilization solution (200 mM NaOH containing 2% NaCl). For each wash, the tubes were mixed after adding the immobilization solution, centrifuged as above for 2.5 minutes and the supernatants were carefully removed by aspiration.

21 mg of Procion Red MX-B5 or Remazol Brilliant Orange 3R dye in 2 ml of immobilization solution was added to the equilibrated agarose pellet, mixed and incubated in a 60° C. water bath with constant mixing by gently rotation for 1 hour.

The reaction was stopped and unbound dye was removed by sequential washing with 10 ml water per wash as above until the wash supernatants were completely clear and colorless. After the final wash supernatant was removed, the colored agarose pellets were suspended in 1 ml Tris buffered saline containing 20% ethanol to give a 50% slurry and stored at 4° C. until use.

100 μl of each 50% resin suspension (50 μl packed gel) was tested directly, or mixed at 10% with non-colored agarose, for the amount of non-specific background protein binding with mammalian tissue culture cell lysates as described in the mock immunoprecipitation protocol of Example 2.

Results:

100% Procion Red MX-5B agarose showed binding of non-specific background protein was reduced by 70-80% compared to control Reactive Red 120 agarose and was comparable to Reactive Red 120 agarose blocked with gelatin and cross-linked with EDAC (see Example 2). 100% Remazol Brilliant Orange 3R agarose showed binding of non-specific background protein was reduced by >95% compared to control Reactive Red 120 agarose. When used as a 10% mixture in agarose, the Remazol Brilliant Orange 3R agarose was still quite visible, but showed no significant difference in binding of non-specific background protein and was comparable to non-colored agarose alone (100% Sepharose CL-4B).

The procedure above demonstrated that we could make a visible agarose resin with the desired visibility, centrifugation, and very low protein binding ability properties necessary for this invention.

EXAMPLE 4

Coupling Reactive Dyes to Agarose Using Carbonate

Another method of coupling dyes to agarose involves carrying out the coupling reaction in a carbonate. For each coupling reaction, 3.5 ml of a 50% slurry of Sepharose CL-4B agarose (1.75 ml packed gel) was dispensed to a tube and was centrifuged in a table top centrifuge 5 minutes at 2500×g at room temperature. Each supernatant was removed by aspiration. The agarose resin pellets were each washed three times with 10 ml water as described in Example 2, and the final wash supernatants were removed by aspiration. The agarose resin pellets were each suspended in 0.5 packed gel volumes (0.85 ml) of 0.4 M sodium carbonate ($Na_2CO_3$).

Procion Red MX-B5 (Aldrich Product #404365) and Remazol Brilliant Orange 3R (Aldrich Product #306509) were each weighed out at 20 mg/ml packed gel (35 mg each) and each was dissolved in 0.5 packed gel volume (0.85 ml) of 0.68 M NaCl. For each coupling reaction, each dye/salt solution (0.85 ml) was added to a tube containing the agarose/carbonate slurry (0.85 ml) from above. Each coupling reaction tube was incubated at 60° C. in a water bath with gentle shaking for thorough and continuous mixing.

Each reaction was stopped, and unbound dye was removed, by centrifugation, aspiration, and sequential washing of the agarose pellets with 10 ml water per wash as above, until the wash supernatants were completely clear and colorless. After the final wash supernatant was removed, the colored agarose pellets were suspended in 1 ml Tris buffered saline containing 20% ethanol to give a 50% slurry and stored at 4° C. until use.

100 µl of each 50% resin suspension (50 µl packed gel) was tested directly, or mixed at 10% with non-colored agarose, for the amount of non-specific background protein binding with mammalian tissue culture cell lysates as described in the mock immunoprecipitation protocol of Example 2.

Results:

The results were very similar to those in Example 3. 100% Procion Red MX-5B agarose showed binding of non-specific background protein was reduced by 70-80% compared to control Reactive Red 120 agarose and was comparable to Reactive Red 120 agarose blocked with gelatin and cross-linked with EDAC (see Example 2). 100% Remazol Brilliant Orange 3R agarose showed binding of non-specific background protein was reduced by >95% compared to control Reactive Red 120 agarose. When used as a 10% mixture in agarose, the Remazol Brilliant Orange 3R agarose was still quite visible, but showed no detectable binding of non-specific background protein and was comparable to non-colored agarose alone (100% Sepharose CL-4B).

This method allowed the preparation of a visible agarose resin with the desired visibility, centrifugation, and very low protein binding ability properties necessary for this invention without requiring alkali solutions.

EXAMPLE 5

Use of Colored Affinity Matrix in an Immunoprecipitation Procedure

Remazol Brilliant Red BB was coupled to agarose (Sepharose CL-4B) using the method described in Example 4. The resulting colored resin, Brilliant Red BB agarose, was tested for the amount of non-specific background protein binding with mammalian tissue culture cell lysates as described in the mock immunoprecipitation protocol of Example 2. 100% Remazol Brilliant Red BB agarose showed binding of non-specific background protein was reduced by >95% compared to control Reactive Red 120 agarose. When used as a 10% mixture in agarose, the Remazol Brilliant Red BB agarose was still quite visible, but showed no significant binding of non-specific background protein and was comparable to non-colored agarose alone (100% Sepharose CL-4B).

The performance of the Remazol Brilliant Red BB agarose as a visualization aid in an affinity based molecular pull down application was assessed in the following immunoprecipitation experiment. The experiment compared 10% Remazol Brilliant Red BB agarose in standard non-colored Protein A agarose (Red Protein A agarose) with 100% standard non-colored Protein A agarose (Sigma Product #P3391; Non-colored Protein A agarose) for immunoprecipitation of a recombinant fusion protein spiked into a lysate of mammalian cells.

COS7 tissue culture cells were grown to confluence in 100 mm tissue culture plates, washed two times briefly with 10 ml ice cold phosphate buffered saline. After the second wash solution was aspirated from the plates, 1 ml of ice cold RIPA lysis buffer was added to each plate and the cells were lysed and harvested with a cell scraper. The lysate was removed from each plate and pooled on ice. 1 ml samples were dispensed to tubes, quick frozen, and put to −70° C. for storage.

100 µl aliquots of a 50% slurry of Red Protein A agarose or Non-colored Protein A agarose were dispensed to 1.5 ml microcentrifuge tubes and washed four times with 750 µl RIPA lysis buffer per wash. After the final wash supernatant was removed, the tubes with the washed agarose resin pellets were set on ice.

Frozen lysates were thawed and set on ice immediately before the experiment. Denatured DNA (in the form of a slimy aggregate) was manually removed from each 1 ml lysate sample with a pipet. 100 µl of mammalian protease inhibitor cocktail (Sigma Product #P8340) was added to each and samples were mixed briefly by vortexing. Cell debris and denatured protein precipitate was removed by centrifugation in a microcentrifuge at 8,000×g for 10 minutes at 4° C. The clear supernatants were carefully removed and transferred to clean tubes for immunoprecipitation.

For half the tubes of cleared lysates, 1.2 µl of 5.4 µg/µl N-terminal FLAG-BAP (Bacterial Alkaline Phosphatase) purified recombinant fusion protein (Sigma Product #P7582) was added to each, mixed gently and set on ice. 3.85 µl of anti-BAP mouse monoclonal antibody BAP-77 (2.6 mg/ml; Sigma Product #B6804) was added to each tube of cleared lysate and mixed gently. The tubes were put to mix by rotation at 4° C. for one hour in order to allow antibody-antigen complexes to form. The tubes were centrifuged for 5 seconds and the entire contents of each were transferred with a pipet to a separate tube of washed agarose resin pellet on ice and briefly mixed. These tubes were put to mix by rotation at 4° C. for one hour to allow antibody-antigen complexes to bind the Protein A agarose.

After the incubation the agarose resins were collected by centrifugation in a microcentrifuge for 30 seconds at 8000×g at 4° C. and the supernatants were removed by aspiration. Each pellet was washed four times with 750 µl ice cold RIPA buffer per wash. For each wash, the pellets were mixed by rotation at 4° C. for 5 minutes, centrifuged as before and the supernatants were aspirated. After the final wash supernatants were removed, 25 µl of RIPA buffer was added to each and mixed briefly. Then 25 µl of 2X Laemmli protein gel sample buffer (Sigma Product #S3401) was added to each, mixed and the resulting samples were boiled for 5 minutes to release the protein from the agarose resins.

The samples were centrifuged briefly to pellet the agarose resins and 10 µl of each supernatant was subjected to SDS/PAGE denaturing gel electrophoresis and analyzed by western immunoblotting. The western blot was probed with anti-FLAG M2 monoclonal antibody conjugated with alkaline phosphatase followed by standard NBT/BCIP calorimetric detection.

Results:

The Red Protein A agarose pellets were highly visible in ambient light, while the Non-colored Protein A agarose pellets were difficult to see. The high visibility of the Red Protein A agarose made all manipulations easier and less prone to error caused by accidental removal of the pellets during aspirations. The Red Protein A agarose immunoprecipitates gave the same signal intensity on the immunoblots for the N-FLAG-BAP protein as the Non-colored Protein A agarose immunoprecipitates with no detectable increase in non-specific background. Thus, the invention significantly facilitated an affinity based molecular pull down application, immunoprecipitation, while providing equivalent performance of the standard procedure.

What is claimed is:

1. An affinity matrix for the isolation of a molecule from an aqueous solution, the affinity matrix comprising a particulate polymeric support material, a dye covalently attached to a fraction of the particles of the polymeric support material to enable optical detection of the polymeric support, and an affinity ligand other than the dye attached to a fraction of the particles of the polymeric support material for the capture of a molecule wherein the affinity matrix comprises particulate polymeric support material to which affinity ligand but not dye is attached.

2. The affinity matrix of claim 1 wherein the particulate material has an average size of less than about 1,000 micrometers.

3. The affinity matrix of claim 1 wherein the dye and affinity ligands are attached to different fractions of the particles of the polymeric support material.

4. The affinity matrix of claim 3 wherein the dye is attached to about 1% to about 50% by weight of the particulate polymeric material and the affinity ligand is attached to about 50% to about 99% by weight of the particulate polymeric material.

5. The affinity matrix of claim 3 wherein the capacity of the affinity matrix to non-specifically bind protein present in the lysate of a naturally-occurring mammalian cell under physiological salt and pH conditions is less than 100 times the capacity of a reference matrix under the same conditions wherein the reference matrix is substantially identical to the affinity matrix except that no dye is bound to any of the particulate material of the reference matrix.

6. The affinity matrix of claim 5 wherein the dye comprises a dye possessing an azo chromophore, a dye possessing an anthroquinone chromophore, or a dye possessing a phthalocyanine chromophore.

7. The affinity matrix of claim 5 wherein the dye comprises a dye possessing a vinyl sulfone, a dye possessing a mono or dichloro triazine, or a dye possessing a monochloro difluoro pyrimidimium.

8. The affinity matrix of claim 1 wherein the affinity matrix is modified by gelatin absorption and cross-linking.

9. The affinity matrix of claim 8 wherein the dye comprises fluorescein, a coumarin derivative, a pyridyloxazole derivative, or a lanthanide metal chelate.

10. The affinity matrix of claim 8 wherein the dye comprises napthalene, pyrene, rhodamine, fluorescein isothiocyanate, a terbium complex, a europium complex, or a ruthenium complex.

11. The affinity matrix of claim 1 wherein the particulate polymeric support comprises natural agarose particles, cross-linked agarose particles, cross-linked dextran particles, or polyacrylamide particles.

12. The affinity matrix of claim 1 wherein the affinity matrix comprises particulate polymeric support material to which dye but not affinity ligand is attached.

13. The affinity matrix of claim 1 wherein the amount of dye that is attached to the polymeric support comprises between about 0.5 micromoles of dye/cm$^3$ of polymeric support to about 20 micromoles of dye/cm$^3$ of polymeric support.

14. The affinity matrix of claim 1 comprising a mixture of a non-colored affinity matrix and a colored polymeric support, the colored polymeric support comprising a polymer and a dye attached to the polymer.

15. The affinity matrix of claim 14 wherein the colored polymeric support comprises between about 1% by volume to about 95% by volume of the affinity matrix.

16. The affinity matrix of claim 14 wherein the non-colored affinity matrix comprises an antibody binding matrix.

17. The affinity matrix of claim 16 wherein the antibody binding matrix is selected from the group consisting of protein A agarose, agarose modified with a molecule with the binding properties of protein A, protein G agarose, agarose modified with a molecule with the binding properties of protein G, protein L agarose, agarose modified with a molecule with the binding properties of protein L, protein A/G agarose, agarose modified with a molecule with the binding properties of protein A/G, protein L/A agarose, and agarose modified with a molecule with the binding properties of protein L/A.

18. The affinity matrix of claim 14 wherein the non-colored affinity matrix comprises a matrix with attached antibodies.

19. The affinity matrix of claim 14 wherein the non-colored affinity matrix comprises a matrix with attached affinity ligands.

20. The affinity matrix of claim 14 wherein the colored polymeric support is distributed substantially uniformly in the non-colored affinity matrix.

* * * * *